United States Patent [19]

Buckman et al.

[11] 4,054,542

[45] Oct. 18, 1977

[54] AMINE-EPICHLOROHYDRIN POLYMERIC COMPOSITIONS

[75] Inventors: John D. Buckman; Stanley J. Buckman; Gerald D. Mercer; John D. Pera, all of Memphis, Tenn.

[73] Assignee: Buckman Laboratories, Inc., Memphis, Tenn.

[21] Appl. No.: 665,664

[22] Filed: Mar. 10, 1976

Related U.S. Application Data

[63] Continuation-in-part of Ser. No. 568,066, April 14, 1975, abandoned.

[51] Int. Cl.$^2$ .............................................. C08G 65/26
[52] U.S. Cl. .................................. 260/2 BP; 8/84; 71/67; 156/331; 162/164 EP; 210/54; 260/29.2 EP; 260/567.6 P; 424/78; 424/329; 428/413
[58] Field of Search ........ 260/2 BP, 29.2 EP, 567.6 P

[56] References Cited

U.S. PATENT DOCUMENTS

| | | | |
|---|---|---|---|
| 3,441,609 | 4/1969 | McKelvey et al. | 260/583 |
| 3,567,659 | 3/1971 | Nagy | 260/2 |
| 3,711,573 | 1/1973 | Nagy | 260/874 |
| 3,725,312 | 4/1973 | Panzer et al. | 260/2 BP |
| 3,738,945 | 6/1973 | Panzer et al. | 260/2 BP |
| 3,819,541 | 6/1974 | Longoria et al. | 260/2 BP |

*Primary Examiner*—Harold D. Anderson
*Assistant Examiner*—E. A. Nielsen
*Attorney, Agent, or Firm*—Floyd Trimble

[57] ABSTRACT

Cationic, water-soluble, amine-epichlorohydrin polymeric compositions formed by reacting polymeric bis(3-chloro-2-hydroxypropyl) amines with tertiary amines are useful in papermaking processes, in water purification processes, textile manufacturing processes, and for the control of pests such as algae, bacteria and fungi.

32 Claims, No Drawings

AMINE-EPICHLOROHYDRIN POLYMERIC COMPOSITIONS

This application is a continuation-in-part of co-pending application Ser. No. 586,066, filed Apr. 14, 1975, now abandoned.

This invention relates to cationic, water-soluble, amine-epichlorohydrin polymer compositions and to the uses of these polymers in the pulp and paper industry to improve drainage, provide retention of fiber fines, dyes, pigments, fillers, starch, and gum and increase strength. In addition, said polymers are useful as resins in the manufacture of electroconductive paper and the sizing of paper and paperboard as well as the separation of minerals in ore processing operations.

The cationic polymers of this invention can also be used to improve aqueous adhesive formulations, as flocculants for the purification of water and the processing of wastes, to improve dyeability and color fastness in textiles, and to increase the adhesion of water-proofing and flame-proofing finishes to fabrics. The cationic polymers of this invention are also effective in controlling the growth of algae, bacteria and fungi in swimming pools and in commercial and industrial cooling and process water.

Cationic polymers have been used in the past in the pulp and paper, textile and water treating industries for the uses described in this invention; but none, however, are entirely satisfactory. Some are useful as retention aids and flocculants but do not provide any of the other desired benefits. Ionene-type polymers which are prepared by reacting di-tertiaryamines with dihalo compounds are typically products with relatively low molecular weights. These products may be effective for controlling microorganisms, but their use as flocculants is limited. The most versatile cationic polymers are the polyethylenimines which can be manufactured in various molecular weight ranges by the selection of different catalysts and the use of cross-linking reagents. None of the polyethylenimines are good microbiocides. In addition, the manufacture of polyethylenimines requires the use of the very toxic monomer ethylenimine which, in recent years, has been described as a carcinogen, and severe restrictions have been placed on the handling of the monomer in commercial and industrial plants by government regulatory agencies.

It is, therefore, a principal object of this invention to provide novel cationic, water-soluble, amine-epichlorohydrin polymers.

It is another object of our invention to provide methods for improving drainage and increasing retention of fines, dyes, pigments, fillers and starch in the papermaking process as well as increasing strength, improving sizing and increasing electrical conductivity of paper and paperboard.

It is yet another object of our invention to provide methods for improving aqueous adhesive formulations.

It is yet another object of our invention to provide methods of flocculating impurities in water and methods of improving processing of wastes.

It is yet another object of our invention to provide methods of improving dyeability and color fastness in textiles and of increasing the adhesion of water-proofing and flame-proofing finishes to fabrics.

It is yet another object of our invention to provide methods of controlling the growth of algae, bacteria and fungi in swimming pools and in commercial and industrial cooling and process water.

These and other objects and advantages of the novel compositions and methods of this invention will become apparent as the description proceeds.

To the accomplishment of the foregoing and related ends, this invention then comprises the features hereinafter fully described and particularly pointed out in the claims, the following descripton setting forth in detail certain illustrative embodiments of the invention, these being indicative, however, of but a few of the various ways in which the principles of the invention may be employed.

The novel cationic, water-soluble, amine-epichlorohydrin polymer compositions have the structure:

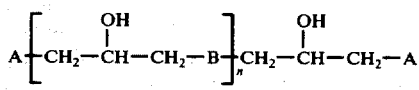

wherein $n$ as used herein and throughout the specification and claims represents an integer; A represents

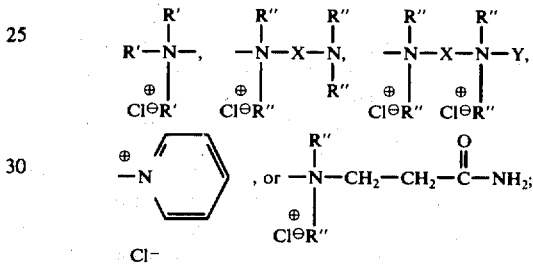

B represents

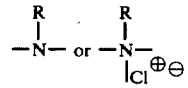

thereby providing for branching in the polymer chain;

X represents a polymethylene group containing 1 to 12 carbon atoms,

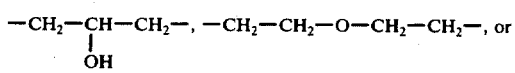

Y represents

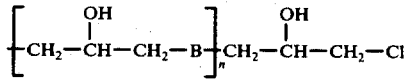

R represents a straight or branched chain alkyl group containing 1 to 20 carbon atoms and 0 to 2 carbon to carbon double bonds, a straight or branched chain alkyl group containing 1 to 6 carbon atoms and one or more hydroxyl or chloro substituents, a saturated aryl group or a benzyl group.

Each of the R' groups independently represents a straight or branched chain alkyl group containing 1 to 20 carbon atoms and 0 to 2 carbon to carbon double bonds, a straight or branched chain alkyl group containing 1 to 6 carbon atoms and one or more hydroxyl substituents, a saturated aryl group, an alkaryl group, or an aryl group;

R" represents a straight chain alkyl group containing 1 to 6 carbon atoms.

The polymers of this invention are prepared using a two-stage reaction procedure. In the first stage, one mole of a primary amine is reacted with two moles of epichlorohydrin or one mole of ammonia is reacted with three moles of epichlorohydrin to produce the polymeric precursor. Similar reactions are described in the chemical literature using water as solvent. However, when water is used, an ill-defined polymeric substance may be obtained, and the ionic chloride developed in the reaction cannot be correlated with the expected products. The reaction is best conducted in the presence of polar solvents such as methanol, ethanol, 1-propanol or 2-propanol. Some water may be present, but the amount of water should be less than the amount of the organic solvent. During the addition of the first mole of epichlorohydrin to the amine solution, the reaction temperature should be below 30° C. The remainder of the reaction may then be conducted at temperatures as high as 60° or 70° C. Primary amines other than the lower alkyl amines require higher temperatures for completion of the reaction. The compound first formed in this reaction is a tertiary amine containing at least two 3-chloro-2-hydroxypropyl substituents. Since compounds of this type contain at least two reactive organic chlorine atoms and a tertiary nitrogen atom, these amines will react with themselves to form branched polymeric quaternary ammonium compounds. This polymerization will occur even at room temperature and is accelerated if the reaction mixture is kept warm. Conventional analytical procedures can be used to follow the decrease in tertiary amine content, and the corresponding increase in ionic chloride as the quaternary ammonium compound is formed.

The tertiary amines formed from one mole of primary amine and two moles of epichlorohydrin or from ammonia and three moles of epichlorohydrin contain at least two active chlorine atoms and only one nitrogen atom. As the quaternization reaction occurs, the polymeric precursor will thus still have available half to two-thirds of the active chlorine atoms for further reaction. In this invention we have found that this polymeric precursor will react with tertiary amines to produce useful water-soluble polymers.

When the precursor is reacted with compounds containing only one tertiary nitrogen, no further polymerization occurs during the second stage since the reaction involves conversion of end group chlorine to quaternary nitrogen chloride. The quantity of monotertiary amine to add will depend on the amount of organic chlorine still available. When a di-tertiary amine is reacted with the polymeric precursor, two or more of the precursor molecules will be joined together when both nitrogen atoms of the di-tertiary amine are quaternized. The amount of branching or cross-linking can be controlled by varying the amount of di-tertiary amine added. If the stoichiometric ratio of tertiary nitrogen atoms to precursor monomer is one or greater than one, less branching or cross-linking will occur. We have found that high molecular weight polymers are produced when the molar ratio of di-tertiary amine to bis(3-chloro-2-hydroxypropyl) amine calculated as the monomer is less than 0.95 to 1. When equimolar ratios are used, lower molecular weight polymers are produced. However, the addition of polymeric precursor to these lower molecular weight polymers to provide a slight molar excess of the precursor will increase the molecular weight of the final product.

The reaction of the polymeric precursor with the tertiary amines is conducted at temperatures between 50° and 100° C. in aqueous solution. The alcoholic solvent used in the precursor reaction may be left in the reaction mixture, but we have obtained our best products by removing the solvent by distillation as the reaction proceeds.

When di-tertiary amines are reacted with the precursor as described herein before, the desired molecular weight will be obtained while unreacted tertiary amine groups are still present. Thus, polymerization will continue to occur even at room temperature over a period of several days. We have found that the polymerization can be stopped at the desired molecular weight by the addition of mineral acids to form a salt of the unreacted tertiary amine.

We have found that the reaction of the polymeric precursor with a di-tertiary amine is facilitated when the reactants are maintained in high concentration. As the polymerization proceeds and the viscosity increases, water is added while heating is continued until the desired viscosity and concentration are obtained. Reaction is stopped by adding sufficient mineral acid to convert all of the unreacted tertiary amine to a salt.

As a further aid for a clear understanding of the nature of the invention, a listing of specific primary amines, tertiary amines containing one tertiary nitrogen and tertiary amines containing two tertiary nitrogen atoms suitable for use in the invention will be given. It should be understood, however, that this listing is merely for the purpose of illustration; and that our invention, as will be apparent to those skilled in the art, is not limited to the use of the specific amines listed.

The primary amines which have been found to be satisfactory for the reaction with epichlorohydrin to form the polymeric precursor include aliphatic, alicyclic, and alkylaromatic amines which may be substituted by hydroxyl or chloro groups or contain carbon to carbon double bonds. The aliphatic groups in these amines may be straight or branched chains. Examples of these amines are as follows:

methylamine;
ethylamine;
n-propylamine;
n-hexylamine;
isopropylamine;
t-octylamine;
stearylamine;
cyclohexylamine;
3-chloro-2-hydroxypropylamine;
benzylamine;
n-butylamine;
s-butylamine;
isobutylamine;
t-butylamine;
tris(hydroxymethyl)methylamine;
ethanolamine;
3-hydroxy-2-methylpropylamine;
isopropanolamine.

Tertiary amines containing one tertiary nitrogen atom which can be reacted with the polymeric precursor include aliphatic, alicyclic, alkylaromatic, aromatic and heterocyclic amines. The aliphatic groups may contain one or more carbon to carbon double bonds and may be substituted with hydroxyl groups. Examples of these amines are as follows:
trimethylamine;
triethylamine;
dimethylstearylamine;
dimethyldecylamine;
dimethyloleylamine;
methyldistearylamine;
(3-chloro-2-hydroxypropyl)dimethylamine;
didecylmethylamine;
dimethylmyristylamine;
N,N-dimethylaniline;
pyridine;
N,N-dimethylbenzylamine;
triethanolamine;
N,N-dimethylethanolamine.

Tertiary amines containing two tertiary nitrogen atoms which can be reacted with the polymeric precursor include the following amines:

N,N,N',N'-tetramethyl-1,2-diaminoethane
N,N,N',N'-tetramethyl-1,3-diaminopropane
N,N,N',N'-tetramethyl-1,3-diaminobutane
N,N,N',N'-tetramethyl-1,4-diaminobutane
N,N,N',N'-tetramethyl-1,6-diaminohexane
N,N,N',N'-tetramethyl-1,3-diamino-2-propanol
N,N,N',N'-tetramethyl-1,4-diaminobutene-2
N,N,N',N'-tetramethylmethylenediamine
bis (beta-dimethylaminoethyl)ether.

Suitable solvents that can be used in the preparation of the polymeric precursor are methanol, ethanol, 1-propanol, 2-propanol, and other polar solvents including mixtures with water. If one wishes to isolate the polymeric precursor, solvents such as hexane, benzene, toluene, or xylene can be used. The polymeric precursor will precipitate and can be removed by filtration.

The cationic polymers of this invention are soluble in water or other polar solvents such as alcohols and dimethylformamide. The molecular weights will vary widely depending on the reaction sequence followed and the end use of the product. For example, the reaction products involving polymeric precursor and monotertiary amines may be as low as 500 whereas the polymers made with di-tertiary amines may have molecular weights as high as 50,000 to 500,000.

This invention provides a process for the preparation of paper or paperboard wherein an aqueous fluid containing cellulosic pulp and other papermaking ingredients is formed into a sheet on a fourdrinier wire cloth, one or more of the polymers of this invention being added to the aqueous fluid before the furnish contacts the fourdrinier wire cloth. Thus, the polymeric compositions of our invention are useful as drainage aids, formation aids, retention aids, sizing agents, and as strength improving agents for paper and paperboard, as well as resins. When these polymers are used as papermaking aids for manufacture of electroconductive paper, one or more of them may, for example, be added continuously to the paper machine system at suitable locations such as the machine chest, the fan pump, or the headbox at concentrations ranging from 0.05 to 2 percent based on the weight of the dry pulp. The desirable results obtained by using these processes may be summarized as follows:

1. Increased production per unit of equipment;
2. Improved formation and strength properties of paper and paperboard;
3. Increase in overall mill efficiency in that losses of dyes, fine fibers, pigments, fillers, starch, and other paper components are minimized by increasing retention of these products in paper and paperboard; and
4. Alleviation of water pollution problems by using the polymers in the recovery of the valuable materials remaining in the process waters of paper and pulp manufacture.

These polymeric compositions can also be used to remove dissolved or solid particulate matter remaining in the water before it is discharged even though such matter is not of a character suitable for use but must be disposed of by microbiological decomposition or combustion, or buried in a sanitary fill.

These polymeric compositions according to the invention are also useful in the treatment of incoming water supplies. These compositions are fast-acting flocculants and will achieve a reduction in process time in addition to the desired degree of completeness in the removal of finely divided or dissolved solids. Similar principles apply to the removal of dissolved and particulate matter from water discharged as industrial or municipal effluents.

According to a further feature of the invention, there is provided a method of flocculating solids from an aqueous system which comprises adding to the aqueous system one or more of these polymers, as herein before described, in an amount sufficient to cause flocculation of the solids. One or more of the water-soluble polymers may be added to a given aqueous suspension with sufficient agitation to insure uniform distribution. Following this treatment, the flocculated aggregates will settle. The amount of the water-soluble polymers necessary to produce the desired result is highly variable depending on the amount and nature of the particulate matter on which an effect is needed as well as the other components of the ionic environment in which the polymers and particulate matter are present. Suitable quantities of the polymers of this invention may vary from as low as 0.1 part per million, based on the total weight of water and particulate matter, to as high as 25 parts per million on the same basis with a preferred range of from 0.5 to 5 parts per million.

In modern sewage treatment plants and in other industrial processes, if it often necessary to separate organic and/or inorganic solids from aqueous solutions by filtration. Most often the suspended solids in these systems bear a negative charge. Therefore, the highly cationic polymers of this invention are readily adsorbed on the particles and cause flocculation and agglomeration of the suspended solids, thus facilitating the separation of these solids from the water.

The cationic nature of the water-soluble polymers also serve to provide increased effectiveness in aqueous adhesive formulations. This is accomplished by utilizing the strong positive charge of the polymers in electrostatic bonds or by utilizing the non-polar bonding characteristics of the polymers to adhesive materials and surfaces that do not actually bear charges strong enough to form electrostatic bonds. For example, the adhesive bond of polyethylene to paper is significantly increased by treating the adhesive that is applied to the paper with small amounts of the cationic polymers of this invention.

In the textile industry, the same effects that make these polymers useful in paper manufacture apply to various operations used for the processing of cotton textiles. The affinity of the polymers for the cellulose as well as for various dyes, pigments, and finishes will improve the retention to the fibers as well as increase the resistance of the treated fabric to leaching and other processes which reduce the effectiveness of the cotton additive. The polymers are less effective in providing these effects with synthetic fibers but the polymers of the invention still possess some utility. In particular, the cationic polymers are useful in providing antistatic properties to synthetic textile products as well as fabrics made from natural fibers.

The degradative effect of microorganisms on organic materials is well known. Elimination or inhibition of growth of bacteria, fungi and algae has been the objective of a large number of research projects and patents. Quaternary ammonium compounds and ionene polymers have found utility for the treatment of water used in various commercial and industrial cooling systems and in swimming pools. We have found that the cationic polymers of this invention are effective against bacteria, fungi and algae in water systems even when used in very low concentrations. The polymers provide excellent effectiveness against microorganisms without excessive foaming. The products are readily water soluble and can be diluted with water to any desired concentrations. Other advantages of these polymers are the long shelf life, the lack of corrosiveness and the relatively low toxicity to warm-blooded animals and humans. Concentrations which are suitable for the control of microorganisms vary from 0.5 to 500 parts per million based on the weight of the water being treated.

In order to disclose the nature of the present invention still more clearly, the following illustrative examples will be given. It is to be understood, however, that the invention is not to be limited to the specific conditions or details set forth in these examples except insofar as such limitations are specified in the appended claims.

EXAMPLE 1

A 100-gallon glass-lined jacketed reactor was charged with 210 pounds of methanol and 75 pounds of an aqueous solution containing 50 percent monomethylamine. The reactor was sealed, the agitator started, and full cooling applied to the jacket using ambient temperature (10°-20° C.) water. Epichlorohydrin, 224 pounds, was charged to the reactor at such a rate that the reaction temperature was maintained between 20° and 40° C. The temperature of the reactor contents was maintained between 20° and 40° C. for 12 hours after the epichlorohydrin addition was completed. The solution was analyzed for ionic chloride following the epichlorohydrin addition and was found to increase from 1.7 percent to 3.4 percent during the 12 hours at 20° to 40° C. The total chloride content of the solution was calculated to be 33.78 percent with one-half of this, or 16.89 percent, available as ionic chloride. The methanol solution of the partially polymerized bis(3-chloro-2-hydroxypropyl)methylamine was cooled to 25° C. and was ready for use in subsequent reactions. The product described in this example is typical of the polymeric precursor discussed in the body of the patent.

EXAMPLE 2

A 5-liter round-bottomed, 4-necked glass reaction flask equipped with external heating or cooling, thermometer, agitator, dry-ice cooled condenser and dropping funnel was charged with 1529 grams of methanol and 549 grams of an aqueous solution containing 50 percent monomethylamine. Epichlorohydrin, 855.3 grams, was added dropwise to the above solution at such a rate that the reaction temperature was maintained between 10° and 30° C. Another 800 grams of epichlorohydrin was then added at a rate that the reaction temperature was maintained between 55° and 60° C. The agitation was continued for three hours after the epichlorohydrin addition was completed at a temperature of 55° to 60° C. The partially polymerized methanol solution of bis(3-chloro-2-hydroxypropyl)methylamine was cooled to 25° C. and was ready for use in subsequent reactions.

EXAMPLE 3

The procedure of Example 1 was followed wherein the organic solvent employed was 1-propanol. The polymeric precursor obtained from this solvent was comparable to that obtained in Example 1 as shown by infrared spectral analysis.

EXAMPLE 4

The procedure of Example 1 was followed with smaller quantities of reagents and solvents wherein the organic solvents used were ethanol, 2-propanol and acetone. The polymeric precursor obtained from these solvents was comparable to that obtained in Example 1 as shown by infrared spectral analysis.

EXAMPLE 5

The procedure of Example 2 was followed wherein the monomethylamine was varied from 35 percent aqueous to 100 percent anhydrous monomethylamine.

EXAMPLE 6

The procedure of Example 2 was followed with smaller quantities of reagents and solvents wherein the monomethylamine was replaced by the following amines:
ethylamine;
n-propylamine;
iso-propylamine;
n-butylamine;
t-butylamine;
t-octylamine;
n-hexylamine;
cyclohexylamine;
ethanolamine;
benzylamine;
stearylamine;
tris(hydroxymethyl)methylamine;
3-hydroxy-2-methylpropylamine;
3-chloro-2-hydroxypropylamine.

EXAMPLE 7

A 100-gallon glass-lined jacketed reactor was charged with 245 pounds of a methanol solution containing 51.4 percent of partially polymerized bis(3-chloro-2-hydroxypropyl)methylamine (prepared as described in Example 1). The reactor was set up for distillation under vacuum. The methanol (approximately 90 pounds) was distilled off under a reduced pressure of 122 mm. to 50 mm. of mercury at the temperature of 40° to 50° C. The reactor was then charged with 53 pounds of water and 103 pounds of an aqueous solution containing 59.14 percent N,N,N',N'-tetramethyl-1,2-diaminoethane. The contents of the reactor were heated at 75° to 95° C. with agitation until the reaction mixture thickened. Water, 430 pounds, was introduced over a period of 1 hour in increments of 33 to 112 pounds to dilute the reactor contents. The reaction mass was allowed to thicken between each incremental addition of water. The reaction temperature was maintained at 90° to 95° C. during the addition of water. The reactor contents were cooled to 30° to 35° C. after the last addition of water. The final product viscosity was 1292 centipoises as measured by a Brookfield viscosimeter. The solution viscosity increased with time, notably to a viscosity of 3000 centipoises after 24 hours and finally to a complete gel in 4 days.

EXAMPLE 8

A 1-liter round-bottomed, 4-necked glass reaction flask equipped with external heating, agitator, thermometer, condenser and addition funnel was charged with 260.5 grams of a methanol solution containing 49.75 percent partially polymerized bis (3-chloro-2-hydroxypropyl)methylamine, 73.1 grams of water, and 93.6 grams of an aqueous solution containing 67 percent N,N,N',N'-tetramethyl-1,2-diaminoethane. The reactor contents with agitation were heated at reflux (75° to 90° C.) and 94.2 grams of methanol were removed by distillation. Water, 320 grams, was added and the reactor contents maintained at 55° to 60° C. until the solution viscosity, measured by a Brookfield viscosimeter, reached 1500 centipoises and then 130 grams of water were added. The reaction mixture was cooled to 25° to 30° C. and the solution pH adjusted to 4.0 with the addition of concentrated sulfuric acid. The final viscosity was 1575 centipoises and remained stable on prolonged standing.

EXAMPLE 9

A one-liter, round-bottomed, 4-necked glass reaction flask equipped with heating mantle, agitator, thermometer, condenser and dropping funnel was charged with 132.2 grams of an aqueous solution containing 96.5 percent partially polymerized bis (3-chloro-2-hydroxypropyl)methylamine, 84.5 grams of water, and 112.8 grams of an aqueous solution containing 59.51 percent N,N,N',N'-tetramethyl-1,2-diaminoethane. The reactor contents were heated at 55° to 80° C. for 2 hours and then 250 grams of water were added over a period of 0.5 hour. The reaction temperature was maintained at 75° to 80° C. for an additional two hours. The solution viscosity was measured to be 90 centipoises. To the reaction mixture was added 6.6 grams of an aqueous solution containing 96.5 percent partially polymerized bis (3-chloro-2-hydroxypropyl)methylamine and the reaction temperature was maintained at 75° to 80° C. for four hours. Water, 96.6 grams, was added and the reactor contents were maintained at 60° to 65° C. for 6.5 hours. The solution pH was adjusted to 4.0 with the addition of 19.6 grams of concentrated sulfuric acid. The final solution viscosity was measured to be 2029 centipoises.

EXAMPLE 10

A one-liter round-bottomed, 4-necked glass reaction flask equipped with heating mantle, agitator, thermometer, condenser and dropping funnel was charged with 134 grams of an aqueous solution containing 97.5 percent partially polymerized bis (3-chloro-2-hydroxypropyl)methylamine (prepared as described in Example 1, with removal of the methanol by distillation); 123 grams of water, and 63 grams of an aqueous solution containing 98.7 percent N,N,N',N'-tetramethyl-1,2-diaminoethane. The reaction mixture was heated at a temperature of 70° to 75° C. for 2 hours and then diluted with 320 grams of water. The reaction mixture was heated at 60° C. for 10 hours and showed an increase in Brookfield viscosity from 105 centipoises to 1865 centipoises. Water, 128 grams, was added to dilute the reaction mixture and the resulting solution cooled to 30° to 35° C. The solution pH was adjusted to 3.85 by the addition of 16.8 grams of 96 percent sulfuric acid. The final viscosity of the product was 1280 centipoises.

EXAMPLE 11

The procedure of Example 8 was used wherein the organic solvent employed was ethanol, 1-propanol or 2-propanol. As these solvents necessarily carry out water during their distillation, water equivalent to that removed in the azeotrope was added back to the reactor. The products obtained from use of these solvents were comparable in all respects to the product obtained in Example 8.

EXAMPLE 12

The procedure of Example 8 was used wherein the polymeric bis (3-chloro-2-hydroxypropyl)methylamine was replaced by a comparable molar equivalent of the following polymeric bis (3-chloro-2-hydroxypropyl)alkyl amines where the alkyl group is as follows:
ethy;
n-propyl;
iso-propyl;
n-butyl;
t-butyl;
3-chloro-2-hydroxypropyl;
stearyl;
benzyl;
cyclohexyl;
3-hydroxy-2-methylpropyl;
tris (hydroxymethyl)methyl;
2-hydroxyethyl.

EXAMPLE 13

The procedure of Example 8 was used wherein the N,N,N',N'-tetramethyl-1,2-diaminoethane was replaced by a comparable molar equivalent of the following di-tertiary amines:

bis (beta-dimethylaminoethyl) ether;
N,N,N',N'-tetramethyl-1,3-diaminobutane;
N,N,N',N'-tetramethyl-1,4-diaminobutane;
N,N,N',N'-tetramethyl-1,6-diaminohexane;
N,N,N',N'-tetramethylmethylenediamine;
1,3-bis(dimethylamino)-2-propanol;
N,N,N',N'-tetramethyl-1,3-diaminopropane;

EXAMPLE 14

The procedure of Example 8 was used wherein the N,N,N',N'-tetramethyl-1,2-diaminoethane was replaced by comparable molar quantities of tertiary amines equivalent to the available organic chlorine content of the polymeric precursor. The following tertiary amines are examples of those used:
triethylamine;
pyridine;
trimethylamine;
triethanolamine;
dimethyl $C_{18}$ to $C_{22}$ alkylamines;
dimethylbenzylamine;
3-chloro-2-hydroxypropyldimethylamine.

EXAMPLE 15

A 3-liter round bottomed, 4-necked glass reaction flask equipped with external cooling, agitator, thermometer, dry-ice cooled condenser and dropping funnel was charged with 1200 ml. of methanol and 36.8 grams of anhydrous ammonia. Epichlorohydrin, 596 grams, was added slowly at such a rate that the temperature was maintained between 0° to 25° C. The reaction mixture was agitated overnight and allowed to slowly warm to room temperature. The partially polymerized tris(3-chloro-2-hydroxypropyl)amine solution was ready for use in subsequent reactions.

EXAMPLE 16

A 250-ml. round-bottomed, 3-necked glass reaction flask equipped with external heating, agitator, thermometer and condenser was charged with 44.3 grams of tris(3-chloro-2-hydroxypropyl)amine, 30 grams of water and 43.5 grams of an aqueous solution containing 60 percent N,N,N',N'-tetramethyl-1,2-diaminoethane. The reactor contents were heated at reflux for 2 hours when the contents gelled to a soft water soluble gel.

EXAMPLE 17

A 500-ml. round-bottomed, 4-necked reaction flask equipped with external heating or cooling, agitator, thermometer, condenser and dropping funnel was charged with 16.0 grams of a methanol solution containing 46.2 percent tris(3-chloro-2-hydroxypropyl)amine, 152 grams of a methanol solution containing 39.37 percent bis(3-chloro-2-hydroxypropyl)dimethylammonium chloride, 46.3 grams of an aqueous solution containing 59.51 percent N,N,N',N'-tetramethyl-1,2-diaminoethane and 76 grams of water. The reactor contents were heated at 75° to 80° C. and 102 grams of methanol removed by distillation. The reactor contents were then heated at reflux for 3 hours and then cooled to 25° C. The product was a viscous pale yellow solution.

EXAMPLE 18

Cationic polymeric compositions of this invention were tested for their effectiveness in the retention of titanium dioxide pigment in a pulp pad following a method described by Britt, K. W., Mechanisms of Retention During Paper Formation, TAPPI 56(10), 46–50 (Oct. 1973).

The furnish used in these tests was a 70/30 blend of bleached hardwood and bleached softwood kraft pulps beaten to a standard Canadian freeness of 370 ml. using a laboratory Valley beater. This slurry was then diluted to 0.6 percent consistency and mixed with titanium dioxide at the rate of 10 percent based on the dry weight of the pulp.

The apparatus used was a dynamic drainage jar which is equipped with an agitator to provide controlled turbulence and high dynamic shear. The dynamic drainage jar consists of two parts. The sample to be tested is added to an upper chamber which has a capacity of one liter. The bottom chamber is an air chamber used to prevent the sample from leaving the upper chamber. The two chambers are separated by a screen coated with electrodeposited nickel and containing conical perforations of 0.003-inch diameter in such number as to provide 14.5 percent open area. The agitator in the upper chamber is a two-inch propeller driven by a variable speed synchronous motor. The speed of the agitator was maintained at 1000 R.P.M. in all of the tests.

In these tests, 500 ml. of the 0.6 percent pulp-TiO$_2$ slurry was mixed with the required amount of polymeric retention aid in the upper chamber. The mixture was agitated one minute and a stopper in the bottom chamber was then removed. The sample then filtered through the screen and after 150 ml. had passed the screen, a sample was collected for analysis. This filtrate contained pulp fines and TiO$_2$ that was not retained on the screen. One hundred grams of the filtrate sample were filtered through Whatman No. 42 paper and the TiO$_2$ in the sample was determined by ashing the filter paper.

The percent improvement in retention was calculated using the following formula:

$$\text{Percent retention} = \frac{(\text{Ash in treated sample, g.} - \text{Ash in untreated sample, g.}) \times 100}{\text{Ash in untreated sample, g.}}$$

This procedure was used to test the polymeric materials described in Examples 7, 8, 9, 12 and 13. The increase in retention was significant in every case, and increases were better or equal to those obtained with commercial retention aids in most instances. The results are tabulated in Table 1.

Table 1

Improvement in retention of titanium dioxide

| Polymer variables | | | | Use rate Pound per ton of pulp | Improvement in retention Percent |
|---|---|---|---|---|---|
| R | R' | R" | X | | |
| CH$_3$ | — | CH$_3$ | (CH$_2$)$_2$ | 0.5 | 19.2 |
| C$_2$H$_5$ | — | CH$_3$ | (CH$_2$)$_2$ | 1.5 | 14.4 |
| n-C$_3$H$_7$ | — | CH$_3$ | (CH$_2$)$_2$ | 1.5 | 24.7 |
| i-C$_3$H$_7$ | — | CH$_3$ | (CH$_2$)$_2$ | 1.5 | 6.5 |
| n-C$_4$H$_9$ | — | CH$_3$ | (CH$_2$)$_2$ | 1.5 | 21.7 |
| t-C$_4$H$_9$ | — | CH$_3$ | (CH$_2$)$_2$ | 1.5 | 9.1 |
| n-C$_{18}$H$_{37}$ | — | CH$_3$ | (CH$_2$)$_2$ | 1.5 | 10.6 |
| C$_6$H$_5$—CH$_2$ | — | CH$_3$ | (CH$_2$)$_2$ | 0.5 | 10.7 |
| C$_6$H$_{12}$ | — | CH$_3$ | (CH$_2$)$_2$ | 1.5 | 14.5 |
| HOCH$_2$CH$_2$ | — | CH$_3$ | (CH$_2$)$_2$ | 1.5 | 27.3 |
| CH$_3$ | — | CH$_3$ | (CH$_2$)$_4$ | 1.5 | 20.4 |
| CH$_3$ | — | CH$_3$ | CH$_2$ | 1.5 | 3.9 |
| CH$_3$ | — | CH$_3$ | (CH$_2$)$_3$ | 1.5 | 28.9 |
| CH$_3$ | CH$_3$, CH$_3$, C$_{18}$H$_{37}$ | — | — | 1.5 | 17.6 |

EXAMPLE 19

The flocculatory properties of the cationic polymers of this invention were determined using a mixture of pulp and clay. The procedure was as follows:

An 800-ml. beaker was charged with 550 ml. of water, and 50 ml. of a slurry containing 0.3 gram of ground wood spruce pulp and 0.5 gram of kaolin clay. The pulp and clay had been dispersed by agitating stock solutions with a Waring blender. A paddle turning at 100 R.P.M. was then inserted into the beaker and a solution of polymer to be tested was added to provide the desired concentration. The mixture was agitated for one minute and the paddles were then slowed to 10 R.P.M. Observations of the settling rates of the clay and pulp were made after one and five minutes. The paddles were then stopped and the mixture allowed to stand for ten minutes before the final observations were made.

This procedure was used to test the polymeric materials described in Examples 7, 8, 9, 12 and 13 as flocculants. The flocculating properties of all of the polymers were significant and in most cases the results were better or equivalent to those obtained with commercial cationic flocculating agents.

EXAMPLE 20

The effect of two of the cationic polymers of this invention on the inhibition of the algae *Chlorella pyrenoidosa* and *Phormidium inundatum* was determined using the procedure described in Example 2 of U.S. Pat. No. 3,771,989. Polymer A was prepared by reacting monomethylamine with two moles of epichlorohydrin to form the precursor polymer which was then reacted with 0.9 molar equivalent of N,N,N',N'-tetramethyl-1,2-diaminoethane as exemplified by the product described in Example 7. Polymer B was prepared by reacting the monomethylamine-epichlorohydrin precursor polymer with dimethyl tallow amine as exemplified in Example 14. The results are tabulated in Table 2.

Table 2

| Inhibition of algae by polymer A and polymer B after 7 days | | | | |
|---|---|---|---|---|
| Active ingredient concentration | *Chlorella pyrenoidosa* | | *Phormidium inundatum* | |
| Parts per million | A | B | A | B |
| 0 | 4 | 4 | 4 | 4 |
| 1 | 0 | 0 | 4 | 2 |
| 3 | 0 | 0 | 1 | 0 |
| 5 | 0 | 0 | 0 | 0 |
| 10 | 0 | 0 | 0 | 0 |
| 15 | 0 | 0 | 0 | 0 |
| 20 | 0 | 0 | 0 | 0 |
| 25 | 0 | 0 | 0 | 0 |

EXAMPLE 21

The effect of the two polymers described in Example 20 on the inhibition of the fungi *Chaetomium globosum* and *Penicillium roqueforti* was determined using the method described in U.S. Pat. No. 3,356,706 which was modified by using a mineral salt solution as substrate instead of paper pulp. The mineral salt solution contains the following ingredients:

| Ingredients | Grams per liter |
|---|---|
| Ammonium nitrate | 3.0 |
| Potassium phosphate, dibasic | 1.0 |
| Potassium chloride | 0.25 |
| Magnesium sulfate | 0.25 |
| Tween 80 | 0.5 |
| Deionized water | to 1000 ml. |

Tween 80 is a polyoxyalkylene derivative of sorbitan monooleate manufactured by ICI America, Wilmington, Delaware.

The results are tabulated in Table 3.

Table 3

| Inhibition of two fungi by two cationic polymers after 7 days | | | |
|---|---|---|---|
| Fungus | Active ingredient concentration Parts per million | Growth Polymer A | Polymer B |
| *Chaetomium globosum* | 0 | 4 | 4 |
| | 1 | 0 | 4 |
| | 3 | 0 | 4 |
| | 5 | 0 | 4 |
| | 10 | 0 | 2 |
| | 15 | 0 | 1 |
| | 20 | 0 | 0 |
| | 25 | 0 | 0 |
| *Penicillium roqueforti* | 0 | 4 | 4 |
| | 1 | 2 | 4 |
| | 3 | 1 | 4 |
| | 5 | 0 | 4 |
| | 10 | 0 | 4 |
| | 15 | 0 | 3 |
| | 20 | 0 | 2 |
| | 25 | 0 | 0 |

EXAMPLE 22

The effect of the two polymers described in Example 20 on the percentage kill of the bacterium *Enterobacter aerogenes* was determined using the method described in U.S. Pat. No. 2,881,070 which was modified using a basal salts solution enriched with glucose as substrate instead of paper pulp.

The basal salts solution contained the following ingredients:

| Ingredients | Grams per liter |
|---|---|
| Sodium phosphate, dibasic | 3.0 |
| Potassium phosphate, dibasic | 2.0 |
| Ammonium chloride | 0.5 |
| Magnesium sulfate | 0.01 |
| Ammonium sulfate | 0.5 |
| Glucose | 4.5 |
| Deionized water | to 1000 ml. |

The solution was adjusted to the desired pH with 1 N sulfuric acid prior to sterilization rather than by addition of buffer salts.

The results are tabulated in Table 4.

Table 4

| Percentage kill of *Enterobacter aerogenes* in a basal salt substrate at pH 6.0 after 18 hours' contact by two cationic polymers | | |
|---|---|---|
| Active ingredient concentration | Percent kill | |
| Parts per million | Polymer A | Polymer B |
| 0.5 | 69 | 0 |
| 1 | 0 | 13 |
| 2 | 96 | 56 |
| 3 | — | 25 |
| 4 | 99.5 | 19 |
| 5 | — | 38 |
| 6 | — | 50 |
| 8 | 99.9 | 57 |
| 10 | — | 95 |
| 20 | 100 | 99.99 |
| 25 | — | 100 |

While particular embodiments of the invention have been described, it will be understood, of course, that the invention is not limited thereto since many modifications may be made, and it is, therefore, contemplated to cover by the appended claims any such modifications as fall within the true spirit and scope of the invention.

The invention having thus been described, what is claimed and desired to be secured by Letters Patent is:

1. A cationic, water-soluble, amine-epichlorohydrin polymer prepared using a two-stage reaction process wherein about one mole of ammonia is reacted with about three moles of epichlorohydrin or about one mole of a primary amine having the formula RNH$_2$ is reacted with about two moles of epichlorohydrin in the presence of a polar solvent comprising an alkyl alcohol containing from 1 to 3 carbon atoms and water, thus forming a polymeric precursor and subsequently reacting said precursor with a tertiary amine having the formula:

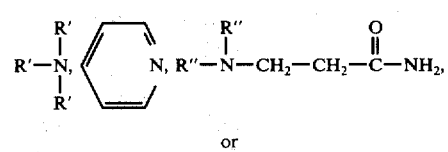

or

-continued

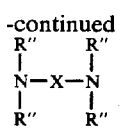

wherein R represents a straight or branched chain alkyl group containing 1 to 20 carbon atoms and 0 to 2 carbon to carbon double bonds, a straight or branched chain alkyl group containing 1 to 6 carbon atoms and one or more hydroxyl or chloro substituents, a saturated aryl group or a benzyl group; and wherein each of the R' groups independently represents a straight or branched chain alkyl group containing 1 to 20 carbon atoms and 0 to 2 carbon to carbon double bonds, a straight or branched chain alkyl group containing 1 to 6 carbon atoms and one or more hydroxyl or chloro substituents, a saturated aryl group, or a benzyl group; R" represents a straight chain alkyl group containing 1 to 6 carbon atoms; X represents a polymethylene group containing 1 to 12 carbon atoms,

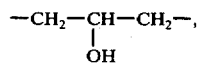

$- CH_2 - CH_2 - O - CH_2 - CH_2 -$; or $- CH_2 - CH=CH - CH_2$; and salts of polymers, having tertiary amine groups.

2. The product according to claim 1 wherein R is a straight or branched chain alkyl group containing 1 to 20 carbon atoms.

3. The product according to claim 1 wherein R is a straight or branched chain alkyl group containing 1 to 6 carbon atoms and one or more hydroxyl or chloro substituents.

4. The product according to claim 1 wherein the primary amine is monomethylamine.

5. The product according to claim 1 wherein the primary amine is ethyl amine.

6. The product according to claim 1 wherein the primary amine is n-propyl amine.

7. The product according to claim 1 wherein the primary amine is iso-propyl amine.

8. The product according to claim 1 wherein the primary amine is n-butyl amine.

9. The product according to claim 1 wherein the primary amine is t-butyl amine.

10. The product according to claim 1 wherein the primary amine is 3-chloro-2-hydroxypropyl amine.

11. The product according to claim 1 wherein the primary amine is stearyl amine.

12. The product according to claim 1 wherein the primary amine is benzyl amine.

13. The product according to claim 1 wherein the primary amine is cyclohexyl amine.

14. The product according to claim 1 wherein the primary amine is 3-hydroxy-2-methylpropyl amine.

15. The product according to claim 1 wherein the primary amine is tris(hydroxymethyl)methyl amine.

16. The product according to claim 1 wherein the primary amine is 2-hydroxyethyl amine.

17. The product according to claim 1 wherein the tertiary amine is N,N,N',N'-tetramethyl-1,2-diaminoethane.

18. The product according to claim 1 wherein the tertiary amine is bis(beta-dimethylaminoethyl) ether.

19. The product according to claim 1 wherein the tertiary amine is N,N,N',N'-tetramethyl-1,3-diaminobutane.

20. The product accordig to claim 1 wherein the tertiary amine is N,N,N',N'-tetramethyl-1,4-diaminobutane.

21. The product according to claim 1 wherein the tertiary amine is N,N,N',N'-tetramethyl-1,6-diaminohexane.

22. The product according to claim 1 wherein the tertiary amine is N,N,N',N'tetramethylmethylenediamine.

23. The product according to claim 1 wherein the tertiary amine is 1,3-bis(dimethylamino)-2-propanol.

24. The product according to claim 1 wherein the tertiary amine is N,N,N',N'-tetramethyl-1,3-diaminopropane.

25. The product according to claim 1 wherein the primary amine is methylamine and the tertiary amine is

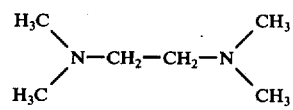

26. The product according to claim 1 wherein the primary amine is methylamine and the tertiary amine is

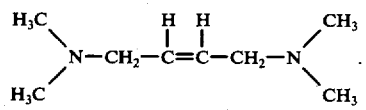

27. The product according to claim 1 wherein the primary amine is a $C_{16}$ alkylamine and the tertiary amine is

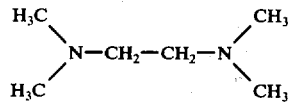

28. The product accordig to claim 1 wherein the primary amine is a $C_{16}$ alkylamine and the tertiary amine is

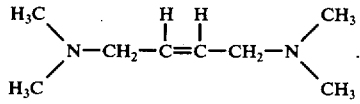

29. The product according to claim 1 wherein the primary amine is a $C_{18}$ alkylamine and the tertiary amine is

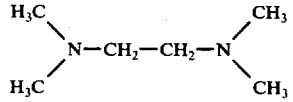

30. The product according to claim 1 wherein the primary amine is a $C_{18}$ alkylamine and the tertiary amine is

31. The product according to claim 1 wherein the primary amine is a $C_{18}$ oleylamine and the tertiary amine is
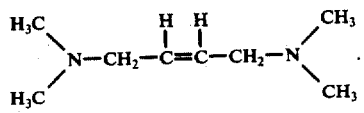
32. The product according to claim 1 wherein the primary amine is a $C_{18}$ oleylamine and the tertiary amine is
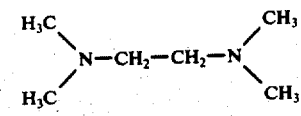
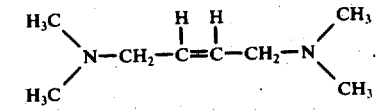
* * * * *